(12) United States Patent
Arcenio et al.

(10) Patent No.: US 8,221,425 B2
(45) Date of Patent: Jul. 17, 2012

(54) PERCUTANEOUS DISCECTOMY AND ENDPLATE PREPARATION TOOL

(75) Inventors: Gregory B. Arcenio, Redwood City, CA (US); Gary A. Schneidermann, Sacramento, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 987 days.

(21) Appl. No.: 12/112,749

(22) Filed: Apr. 30, 2008

(65) Prior Publication Data

US 2009/0275951 A1 Nov. 5, 2009

(51) Int. Cl.
*A61B 17/00* (2006.01)

(52) U.S. Cl. ............................................. 606/84; 606/79
(58) Field of Classification Search .................... 606/79, 606/83–85
See application file for complete search history.

(56) References Cited

U.S. PATENT DOCUMENTS

| 5,697,889 | A | * | 12/1997 | Slotman et al. | ................ | 600/204 |
| 5,755,661 | A | * | 5/1998 | Schwartzman | ................ | 600/216 |
| 2004/0215197 | A1 | * | 10/2004 | Smith et al. | ...................... | 606/79 |

* cited by examiner

*Primary Examiner* — Nicholas Woodall

(57) ABSTRACT

Surgical instruments and surgical methods associated therewith are described. The surgical instruments described herein can be used for scraping or for other purposes such as measuring distances between two points in hard to reach locales.

14 Claims, 9 Drawing Sheets

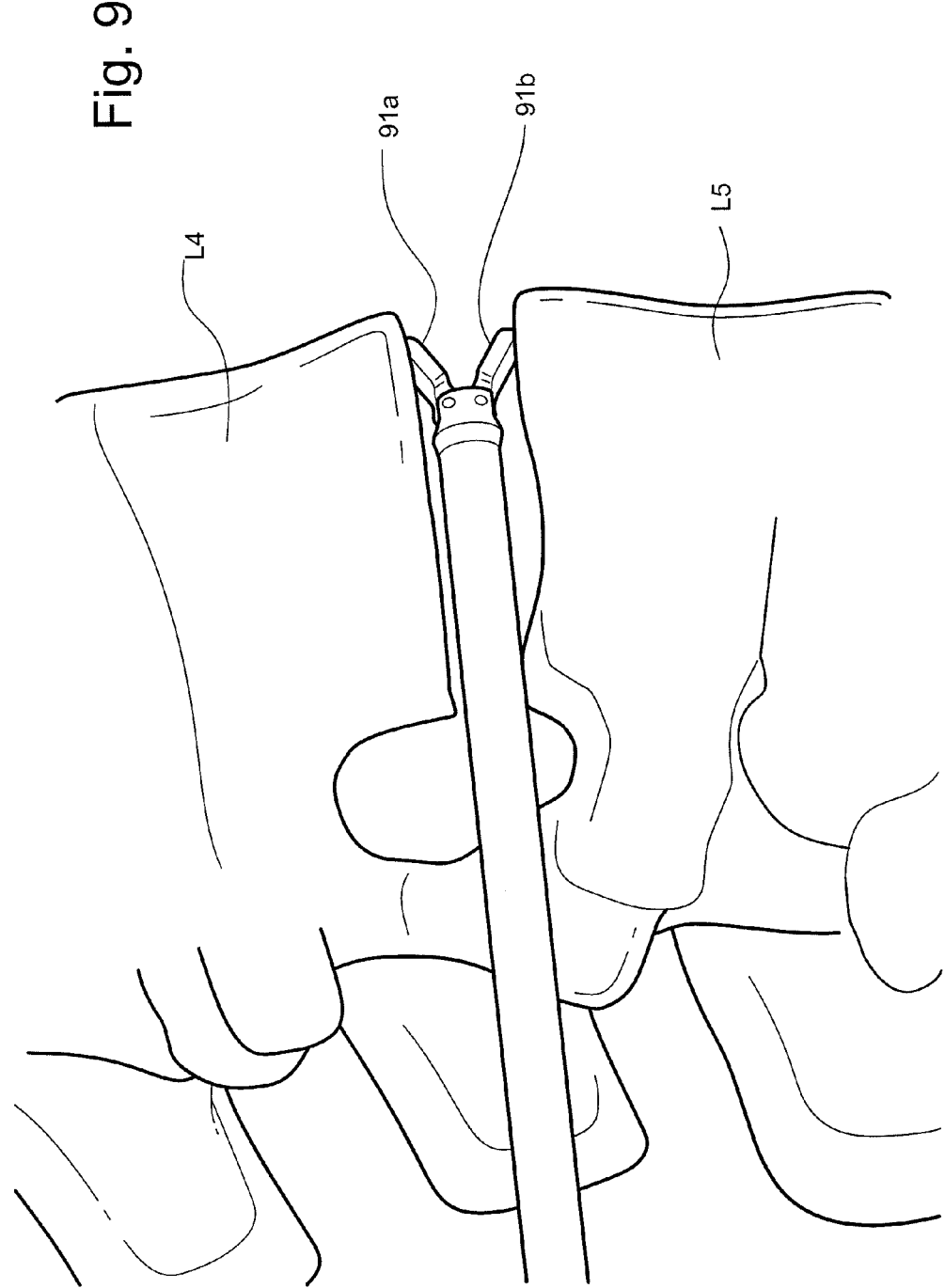

US 8,221,425 B2

PERCUTANEOUS DISCECTOMY AND ENDPLATE PREPARATION TOOL

FIELD OF THE INVENTION

Surgical instruments and associated methods for performing surgery using the surgical instruments are described. An embodiment relates to surgical instruments that can be used for non-invasive surgery wherein the instruments can be used for a plurality of purposes including but not limited to scraping or measuring distances.

BACKGROUND OF THE INVENTION

Traditional surgical procedures for pathologies located deep within the body can cause significant trauma to the intervening tissues. These open procedures often require a long incision, extensive muscle stripping, prolonged retraction of tissues, denervation and devascularization of tissue. Most of these surgeries require recovery room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention.

Minimally invasive alternatives such as arthroscopic techniques reduce pain, post-operative recovery time and the destruction of healthy tissue. Orthopedic surgical patients have particularly benefited from minimally invasive surgical techniques. The site of pathology is accessed through portals and cannulas rather than through a significant incision thus preserving the integrity of the intervening tissues. These minimally invasive techniques can often be performed with only a local anesthetic. The avoidance of general anesthesia reduces post-operative recovery time and the risk of complications.

Minimally invasive surgical techniques are particularly desirable for spinal and neurosurgical applications because of the need for access to locations deep within the body and the danger of damage to vital intervening tissues. For example, a common open procedure for disc herniation, laminectomy followed by discectomy requires stripping or dissection of the major muscles of the back to expose the spine. In a posterior approach, tissue including spinal nerves and blood vessels around the dural sac, ligaments and muscle must be retracted to clear a channel from the skin to the disc. These procedures normally take at least one-two hours to perform under general anesthesia and require post-operative recovery periods of at least several weeks. In addition to the long recovery time, the destruction of tissue is a major disadvantage of open spinal procedures. This aspect of open procedures is even more invasive when the discectomy is accompanied by fusion of the adjacent vertebrae. Many patients are reluctant to seek surgery as a solution to pain caused by herniated discs and other spinal conditions because of the severe pain sometimes associated with muscle dissection.

In order to reduce post-operative recovery time and pain associated with spinal and other procedures, micro-surgical techniques have been developed. For example, in micro-surgical discectomies, the disc is accessed by cutting a channel from the surface of the patient's back to the disc through a small incision. An operating microscope or loupe is used to visualize the surgical field. Small diameter micro-surgical instruments are passed through the small incision and between two laminae and into the disc. The intervening tissues are disrupted less because the incision is smaller.

Fusion of the vertebral bodies involves preparation of the exposed endplate surfaces by decortication (scraping the superior and inferior endplates of the cortical bone) and the deposition of additional bone into disc space between the prepared endplate surfaces. Alternatively, other material may be added during fusion such as bone cements or fusion cages. The complete discectomy and fusion may be performed through a posterior surgical route (from the back side of the patient) or an anterior surgical route (from the front side of the patient). The removed vertebral bone may be just the hard cortical bone or may include soft cancellous soft bone in the interior of the vertebral bodies.

Previously used decortication tools had any of a number of flaws. Most of the decortication instruments are of a size that will not allow them to fit into the cannulas that are used to perform non-invasive procedures. Other tools that are small enough in size to be used in non-invasive procedures are unable to decorticate the superior and inferior endplates simultaneously or they require the surgeon to bias its cutting edge against a particular endplate while scraping the adjacent endplate.

Likewise, the tools that are presently available tend to be designed for open surgeries and require a sizeable surgical exposure to be used effectively. In addition, current instruments require the user to bias the shaft of the instrument against one of the endplates (superior or inferior) while simultaneously dragging the cutting edge across the opposite endplate. In this way, the current instruments require the user to use the opposite endplate as a fulcrum to provide adequate leverage to bias the scraping edge of the instrument against the endplate being scraped. Consequently, only one endplate can be decorticated at a time. Due to this limitation in their use, current endplate preparation instruments are not ideally suited for a percutaneous fusion procedure since the access in this new type of surgery is through a fairly narrow tube, and the ability of the user to bias the instrument against one of the endplates is severely limited.

A surgical instrument that is able to decorticate adjacent endplates at the same time will greatly reduce surgical time. An apparatus that is able to decorticate two adjacent endplates at the same time will often reduce the decortication time by more than half as the surgeon is no longer required to bias the instrument against one endplate while scraping the other, invert the instrument, bias it against the other endplate, and scrape the other endplate. Thus, an instrument that can pass easily through a cannula, can decorticate adjacent endplates simultaneously, biases the instrument equally against the two adjacent endplates and will allow decortication to occur evenly with limited scraping time would be highly desired.

BRIEF SUMMARY OF THE INVENTION

In one embodiment, an expanding endplate scraper instrument that can be used to prepare the endplates during interbody fusion surgery is described. The instrument allows the user to simultaneously prepare (scrape off nucleus material) from both the superior and inferior endplates of a given disc level. Existing instruments for this purpose typically are designed for open surgeries and require a sizeable surgical exposure to be used effectively. The instruments as described herein solve these problems in a number of ways. The instruments can be designed to fit and be effectively used through a 6 mm ID tube. In addition, one embodiment is comprised of dual scrapers that expand in both the inferior and superior directions. The surgical instruments as described simultaneously contact both the superior and inferior endplates of a given disc level. In this way, the contact of each scraper to its endplates biases the opposite scraper against its endplate. In effect, the contact of the superior scraper against the superior endplate biases the inferior scraper against the inferior endplate, and vice versa. As a result, the user is not required to manually bias the instrument against one of the endplates while scraping. This will allow the user to use smaller access tubes (e.g., cannulas). The user can deploy the instrument once it passes through the access tube and the distal end reaches a point between the endplates. Pulling back on the instrument allows the user to effectively scrape both endplates simultaneously. The instruments as described provide significant advantages in speed, ease of use, effectiveness, and safety for percutaneous interbody fusion procedures. However, it should be understood that the instruments as described are not limited to percutaneous procedures and the instruments as described can offer similar benefits to both open and minimally invasive spinal (MIS) fusion procedures.

BRIEF DESCRIPTION OF THE SEVERAL VIEWS OF THE DRAWING(S)

FIG. 9 shows a perspective view of the distal end of the instrument between two adjacent vertebrae.

DETAILED DESCRIPTION OF THE INVENTION

Figure 1:
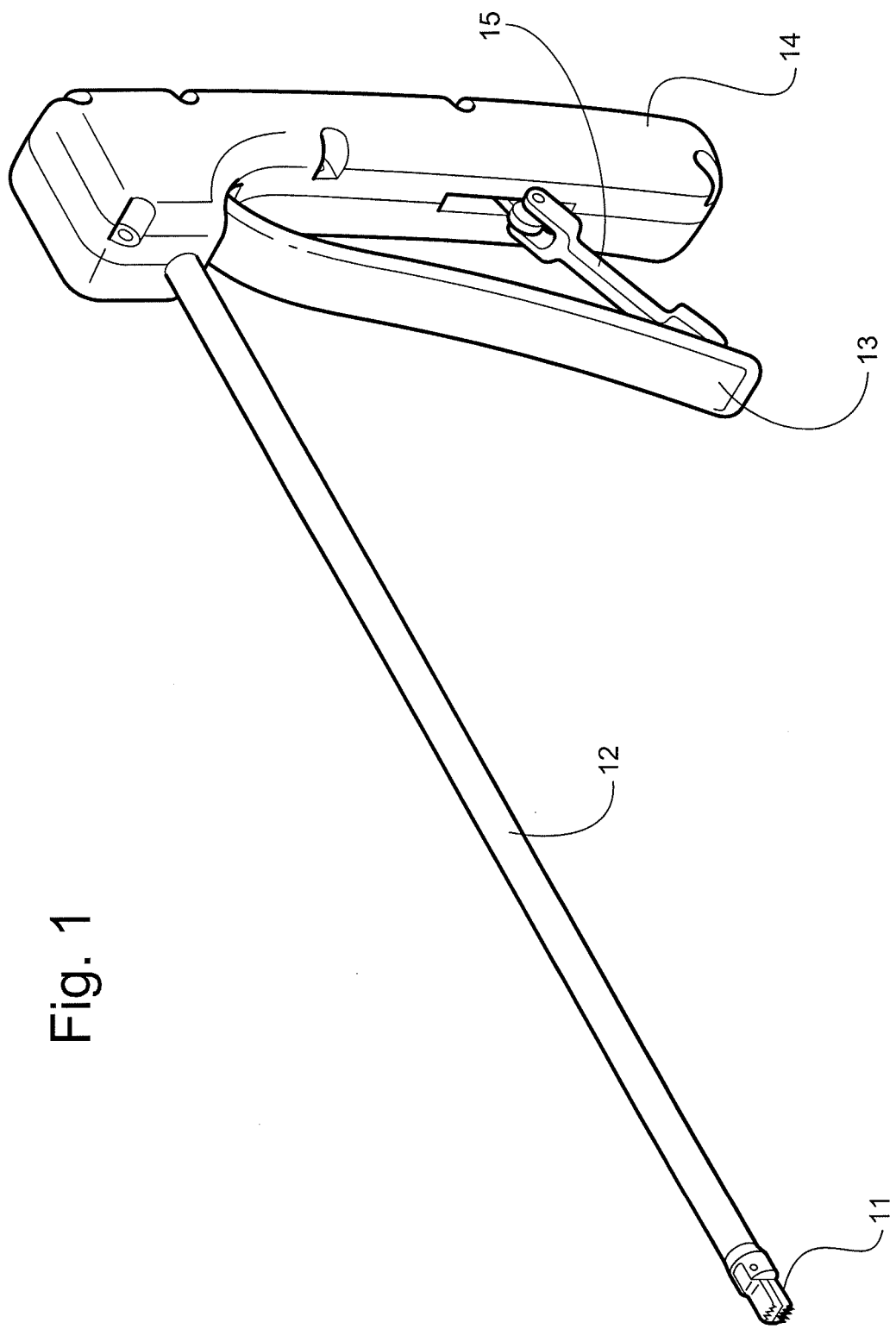
FIG. 1 shows a perspective view of an embodiment with the scraper tips in their closed position and the actuation lever in its open state.

One embodiment of the invention relates to expanding instruments. In a variation of this embodiment, the expanding instrument is an endplate scraper surgical instrument. One use of this surgical instrument is to prepare the endplates during interbody fusion surgery. The instrument allows the user to simultaneously prepare (scrape off nucleus material from) both the superior and inferior endplates of adjacent vertebrae. One advantage that the described instrument has over existing instruments is that it does not require the operator (e.g., a surgeon) to generate sizeable surgical exposure to be used effectively. Rather, in an embodiment, an instrument can pass through an access channel (such as a cannula) that has an inner diameter of 6 mm or smaller. Another advantage of the present instrument is that it allows simultaneous scraping of a first and second endplate because a first end plate is biased against the second endplate while simultaneously biasing the second endplate against the first. Thus, it should be apparent that the instruments as described herein are well-suited for certain types of surgery such as a percutaneous fusion procedures. Because these types of surgery are generally performed through a narrow tube, it is advantageous to have an instrument that can pass through the tube (e.g., a cannula) in an unexpanded state and then allow the user to expand the instrument when it is at or near the surgical location. When performing fusion surgery, the instruments as described herein are also well-suited for this type of surgery as the instruments allow the user to simultaneously bias the instrument against two adjacent endplates.

In an embodiment, a surgical instrument is comprised of dual scrapers that expand in both the inferior and superior directions. In a variation of the embodiment, the scrapers are designed so that they simultaneously contact both the superior and inferior endplates of a given disc level. In this way, the contact of each scraper to its endplates biases the opposite scraper against its endplate. In effect, the contact of the superior scraper against the superior endplate biases the inferior scraper against the inferior endplate, and vice versa. As a result, the user is not required to manually bias the instrument against one of the endplates while scraping. The user can simply deploy the instrument between the endplates and simply pull back to effectively scrape both endplates simultaneously. This provides significant advantages in speed, ease of use, effectiveness, and safety for percutaneous interbody fusion procedures. However, it should be understood that any of a plurality of surgical procedures can be done by this instrument such as both open and MIS fusion procedures. Moreover, the instruments as described herein can access the surgical site from any of a plurality of directions. For example, the surgical instruments may access the surgical site from the posterior route, or from the anterior route, or alternatively, from either or both sides (such as in a circumferential fusion procedure).

As described above and below, the expanding endplate scraper instrument is used to prepare the endplates during interbody fusion surgery. The scrapers simultaneously contact both the superior and inferior endplates of a given disc level Embodiments may be directed to surgical instruments and various methods.

In one embodiment, the instrument comprises an actuation mechanism, a handle, a shaft, and scraper tips. The handle is functionally connected to and positioned at a proximal end of the shaft and the scraper tips are positioned at a distal end of the shaft, and the actuation mechanism causes the scraper tips go from a position that is substantially closed (i.e., tips close to each other) to a position that is substantially open (i.e., the distal tip ends spread apart). In a variation of this embodiment, the instrument further comprises an actuating mechanism containing a push rod and one or more actuation links, wherein the actuation lever is functionally connected to the push rod so that when the actuation lever is compressed the push rod, which is inside the shaft moves in a horizontal direction, causing the one or more actuation links to also move in a horizontal direction, which causes the scraper tips to rotate from a position that is substantially parallel to the shaft to a position that is not parallel to the shaft. In an embodiment the instrument comprises two actuation links.

In a further embodiment, the scraper tips are interchangeable. In alternate embodiments, the scraping tip may be made of a material that is satisfactory for its surgical purpose (i.e., scraping). These materials may include stainless steel, various nickel-titanium alloys (such as NITINOL) as well as other metal alloys that may be suitable for surgical purposes. In alternative embodiments, the scraping tip may be constructed of hard plastics that are reusable or alternatively, may be disposable. In other embodiments, the tips can be different from one another (e.g., one scraping tip and one non-scraping tip, or one serrated tip and one flat tip, or any other combination).

In a further embodiment, the instrument comprises one or more pivot points, the one or more pivot points serving as an axis of rotation for the scraper tips. In one variation, the instrument has two pivot points. In a variation, the pivot points contain a means for removing the scraper tips. One way that the scraper tips may be removed is by devices similar to watch band pins that when depressed allow the scraper tips to be removed. Alternate scraper tips or other tips can then be placed at the distal end of the shaft. Removal of the tips will allow the tips to be cleaned (e.g., the tips can be autoclaved).

In an embodiment, the instrument comprises a first and a second scraper tip, wherein the first and second scraper tips rotate from a position that is substantially parallel to the length of the shaft to a position wherein the first scraper tip rotates between about 1 and 30 degrees relative to the length of the shaft and the second scraper tip rotates between about −1 and −30 degrees relative to the length of the shaft. In a variation, the first and second scraper tips might rotate as much as 60 degrees and −60 degrees, respectively. Compressing the actuation lever causes the scraper tips to rotate in opposite directions (i.e., one scraper tip rotates clockwise and the other rotates counter clockwise). The actuation lever can be slightly compressed so that the scraper tips achieve positions that are less than the fully opened position (i.e., the scraper tips are extended outward as far as they can go).

In another embodiment, the instrument comprises an actuation lever, a handle, a shaft, and tips. The actuation lever is connected to the handle, the handle is functionally connected to and positioned at a proximal end of the shaft and the tips are positioned at a distal end of the shaft, the tips are made of a first and a second tip so that when the actuation lever is compressed, the first tip and the second tip go from a position that is substantially parallel to a length of the shaft to a position wherein the first tip rotates between about 1 and 30 degrees relative to the length of the shaft and the second tip rotates between about −1 and −30 degrees relative to the length of the shaft. In a variation, the first and second scraper tips might rotate as much as 60 degrees and −60 degrees, respectively.

In one embodiment, the first tip and second tips are a first scraper tip and a second scraper tip, respectively, and the first scraper tip and the second scraper tip have serrated edges. Alternatively, the tips may exist in any of a plurality of other conformations. For example, the tips include solid non-serrated scraper tips, the hollow center scraper tips, non-serrated tips and hollow center, serrated tips. The size of the tips may range as is required by the surgical procedure. Thus, in certain non-limiting embodiments, the tips used may range from 0.5-25 mm in length, or from about 1-15 mm in length.

Alternatively, the tips may not be used for scraping but may actually inform the user with information like the distance between two objects. As an example, a surgeon may want to know the distance between the lumbar vertebrae L2 and L3. The surgeon would place tips at the distal end of the shaft that could be used to measure the distance between L2 and L3. The surgeon would compress the actuation lever until the two tips abut against the L2 and L3 vertebrae (i.e., one tip would abut against the L2 vertebra and the other tip would abut against the L3 vertebra). One might calibrate the actuation lever so that the amount that the actuation lever is compressed gives information about the distance between the two vertebrae. In one embodiment, the information may appear as a read-out on a computer screen. Alternatively, the read out may appear on the handle of the instrument. It is contemplated that the read-out may be a result of either electronic or mechanical signals.

In an embodiment, the instrument might further comprise a push rod and one or more actuation links, wherein the actuation lever is functionally connected to the push rod, the push rod is functionally connected to the one or more actuation links, and the actuation links are functionally connected to the scraper tips, so that when the actuation lever is compressed, the first tip rotates relative to the length of the shaft and the second tip rotates in the opposite direction relative to the length of the shaft. The first and second tips can rotate up to 90 and −90 degrees so that they are perpendicular to the length of the shaft. Other maximal rotation amounts are contemplated such as 30 and −30 degrees or 60 and −60 degrees relative to the length of the shaft.

In another embodiment, the instrument may be part of a spinal surgery kit which comprises one or more members selected from the group consisting of a cannula, an instruction manual, bone cement, expandable balloons, interchangeable tips and other surgical instruments.

If a cannula is included as part of a kit, the inner diameter of the cannula should be able to easily accommodate the surgical instruments that are used, including the surgical instrument as described herein, and other surgical instruments such as balloons, bladders, expandable elements, endoscopes, scalpels, screws (e.g., pedicle screws), plates, tamping devices, discs, and other tools that are used in surgical procedures.

Other surgical instruments that may be part of a kit include forceps, retractors, scissors, probes, stylets, knives, speculas, needles, clamps, hammers, suction tubes, spreaders, razors, hooks, pins, resection tools, clips, catheters, and other tools.

In alternate embodiments, methods are also contemplated, One variation is a method of scraping a body region comprising inserting inside a body scraping tips that are positioned on a distal portion of a shaft that is functionally connected to a handle, wherein the scraping tips are substantially parallel to a length of the shaft, actuating the scraping tips to rotate to a position that is not substantially parallel to the length of the shaft, and pulling the handle, which pulls the shaft and the scraping tips so that the scraping tips scrape the body region. In a variation of this method, the body region is an intervertebral disc space.

The method of scraping might employ the instrument as described above. For example, the scraping tips might comprise a first scraping tip and a second scraping tip, the first scraping tip biasing the second scraping tip against an endplate in the intervertebral disc space and the second scraping tip biasing the first scraping tip against a different endplate in the intervertebral disc space. For example, a surgeon might use the inferior endplate of one vertebra to bias one scraping tip while simultaneously using the superior endplate of an adjacent vertebra to bias the other scraping tip.

In an embodiment, the method might employ an instrument that further comprises an actuation lever, a push rod and one or more actuation links, wherein the actuation lever is connected to the handle and operationally connected to the push rod, the push rod is operationally connected to the actuation links so that when the actuation lever is compressed, the push rod moves in a horizontal direction causing the actuation link to move in a horizontal direction, thereby rotating the scraping tips from a position that is substantially parallel to the length of the shaft to a position that is not substantially parallel to the length of the shaft.

After scraping has been successfully completed, the method might also involve releasing the actuation lever thereby rotating the scraping tips from a position that is not substantially parallel to the length of the shaft to a position that is substantially parallel to the length of the shaft. This would allow the user to withdraw the instrument through the lumen of a cannula without having to be concerned that the scraper tips would impede the instruments passage through the lumen.

In alternate embodiments of the method, the instrument might have tips that are made of a material that is satisfactory for its surgical purpose (i.e., scraping). These materials may include nickel titanium alloys (e.g., NITINOL®), stainless steel, silicone and metal materials, superelastic and martensitic materials, tantalum, platinum, and titanium, niobium alloys, PHYNOX®, or any of a plurality of polymeric materials, such as expanded polytetrafluoroethylene (ePTFE), or other materials that may be suitable for surgical purposes. In alternative embodiments, the tip may be constructed of hard plastics that are reusable or alternatively, may be disposable.

In an embodiment, the method may further comprise passing the surgical instrument through a cannula. Alternatively, the method uses the surgical instrument at the surgical site and is not passed through a cannula. In another alternative, the method comprises using the surgical instrument as the cannula.

In one variation, the method may have the surgical site checked with an endoscope to see if sufficient scraping has occurred. The endoscope can also be a part of the instrument so that the shaft does not have to be removed from the surgical site. In a variation of this embodiment, one or more fiber optic cables may pass through the lumen of the shaft, which will allow the surgeon to "see" the operation site, and allow the surgeon to ascertain if sufficient scraping has occurred.

Materials used for the shaft may include stainless steel, nickel-titanium alloys (such as NITINOL), other metal alloys, and hard polymeric plastics. The actuation lever and the handle might also be made of any of these materials.

Several of the embodiments are described in more detail below with reference to the figures.

Figure 2:
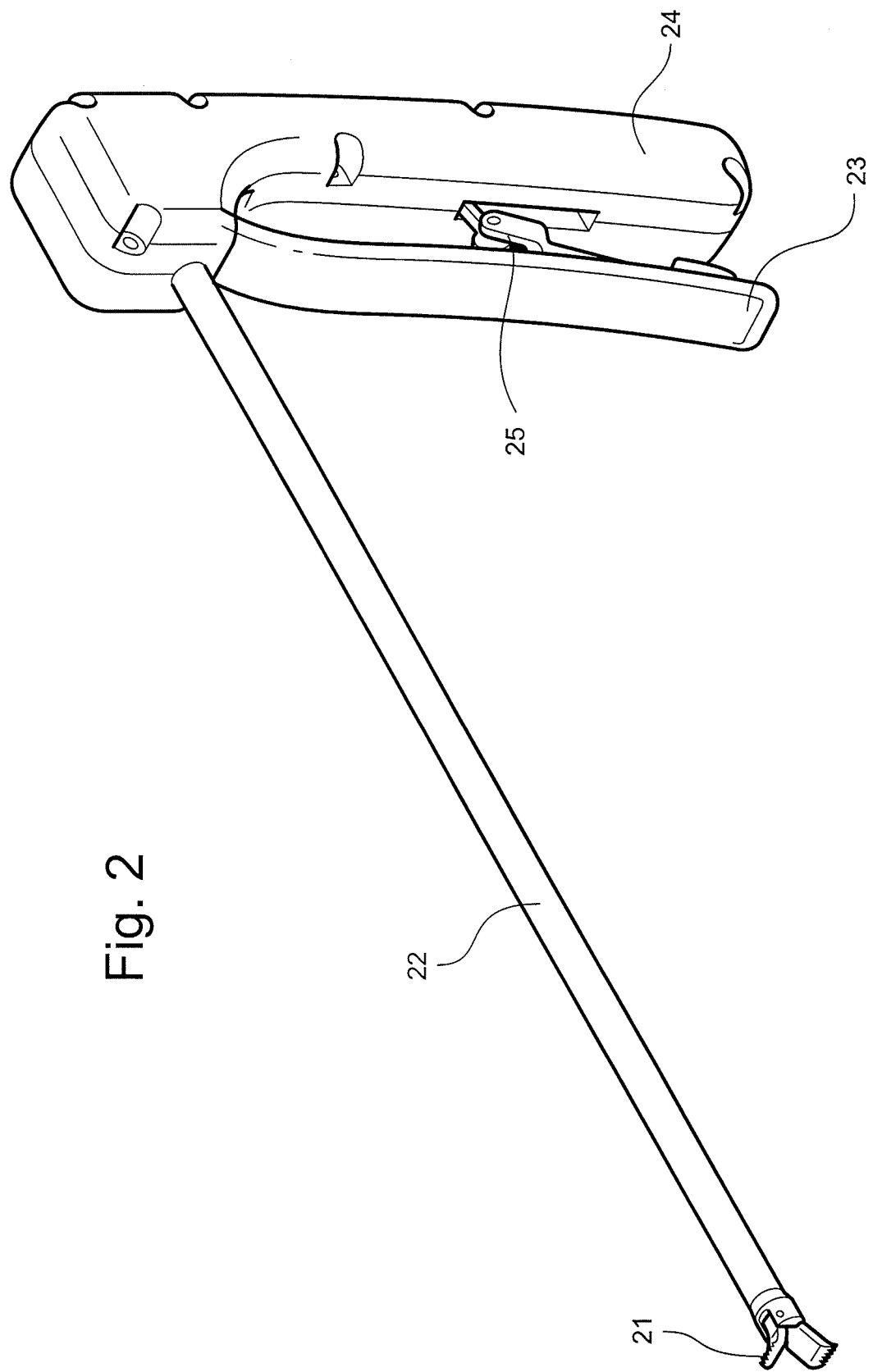
FIG. 2 shows a perspective view of an embodiment with the scraper tips in their fully open position and the actuation lever in its constricted state.

FIG. 1 shows a perspective view of an embodiment with the scraper tips 11 in their closed position and the actuation lever 13 in its open state. Note that the shaft 12, which is attached to the scraper tips 11 can be of a dimension so that it can easily be used in non-invasive surgical procedures. In one variation, the scraper tips 11 in the closed position allow the shaft 12 and the scraper tips to be passed through a narrow passage such as a cannula of 6 mm ID (Inner Diameter) to arrive at the surgical site. When the scraper tips 11 reach the surgical site they can be actuated into the open position by depressing the actuation lever 13. Inside the shaft 12 is an actuation mechanism which allow the scraper tips 11 to go from a closed position as shown in FIG. 1 to an open position as shown in FIG. 2 (embodiments of an actuation mechanism can best be seen in FIGS. 5 and 6). The actuation lever 13 and handle 14 are in an ideal configuration such that a user can use one hand to compress the actuation lever 13 to actuate the scraper tips 11 so that they achieve the open position. In a variation of this embodiment, the scraper tips 11 can open to any of a plurality of positions depending on the amount that the actuation lever 13 is compressed. For example, compressing the actuation lever 13 to a position that is halfway between the "open" and "closed" state will cause the scraper tips 11 to be open to a position that is halfway between the scraper tips "closed" and "open" states.

FIG. 2 shows a perspective view of an embodiment of the present invention with the scraper tips 21 in their fully open position and the actuation lever 23 in its compressed state. Note that the complete compression of actuation lever 23 puts the scraper tips 21 into their fully open state. Although not shown in FIG. 2, it should be understood that compressing the actuation lever 23 into a state that is neither completely open nor completely compressed will result in the scraper tips 21 being in a state that is neither completely closed nor completely open. The compression of the actuation lever 23 moves the adjoining piece 25 (better seen in FIG. 1 as 15), which in turn causes the actuation mechanism (not shown in FIG. 2) present in shaft 22 to cause the scraper tips 21 to open. In an embodiment the scraper tips 21 open at the same time and rate. The scraper tips 21 are of a length that makes them ideally suited for the purpose for which they are to be used. In one use, the tips are to be used to scrape the endplates of vertebrae. Accordingly, when the instrument is used for this purpose, the length of the scraper tips 21 are of a size that allows them to open to a position that allows one scraper tip to be biased against the other allowing the scraper tips to simultaneously scrape the adjacent endplates (e.g., one scraper tip scrapes the inferior endplate on the upper vertebra (for example, L2) and the other scraper tip scrapes the superior endplate on the lower vertebra (for example, L3)).

Figure 3:
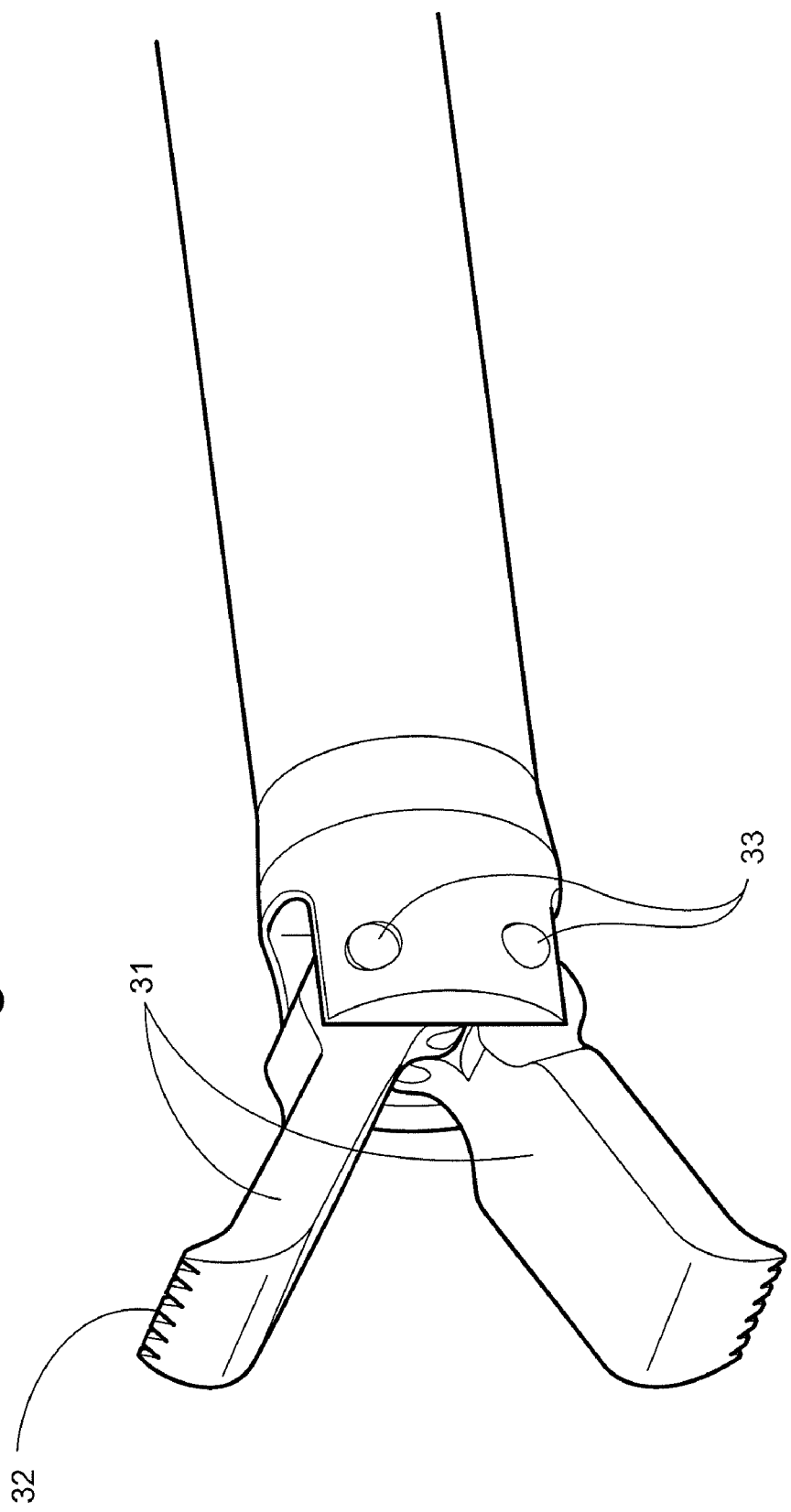
FIG. 3 shows a perspective and close up view of the scraper tips in their open position.

FIG. 3 shows a perspective and close up view of the scraper tips 31 in their open position. In an embodiment (as represented in this figure), the scraper tips 31 may have serrated edges 32 that allow the scraper tips 31 to provide more aggressive scraping. It should be understood that the scraper tips 31 may have any of a plurality of types of serrated edges depending on the depths of the grooves desired. In an embodiment, the scraper tips 31 are interchangeable with other scraper tips. The axis of rotation of scraper tips 31 are pivot points 33. In an embodiment, pivot points 33 provide an avenue for the removal of scraper tips 31 and replacement by other scraper tips. In one variation, the pivot points 33 may comprise devices similar to watch band pins that when depressed allow the scraper tips 31 to be removed.

Figure 4:
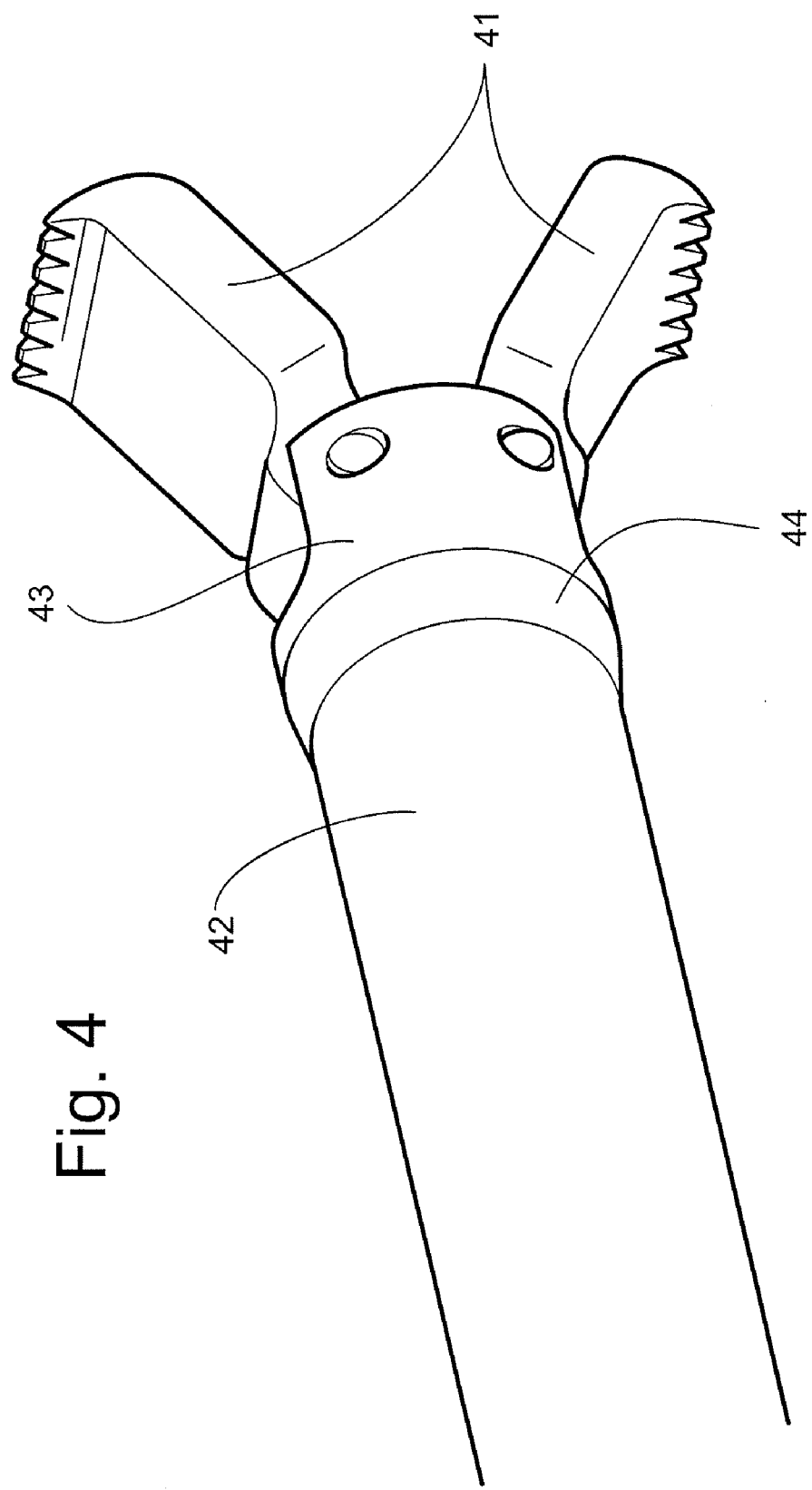
FIG. 4 shows another perspective and close up view of the scraper tips in their open position and a perspective view of the taper.

FIG. 4 shows another perspective and close up view of the scraper tips 41 in their open position and a perspective view of the taper 44. As noted previously, in one embodiment, the scraper tips 41 move in unison when the actuation lever (not shown in FIG. 4) is compressed by means of the actuation mechanism which is present inside shaft 42. In one embodiment, the diameter of shaft 42 is smaller than the diameter of distal portion 43. Accordingly, taper 44 allows a smooth progression from the smaller diameter of shaft 42 to the slightly larger diameter of distal portion 43. The taper 44 eases retraction of the instrument back into the cannula after the requisite scraping is performed.

Figure 5:
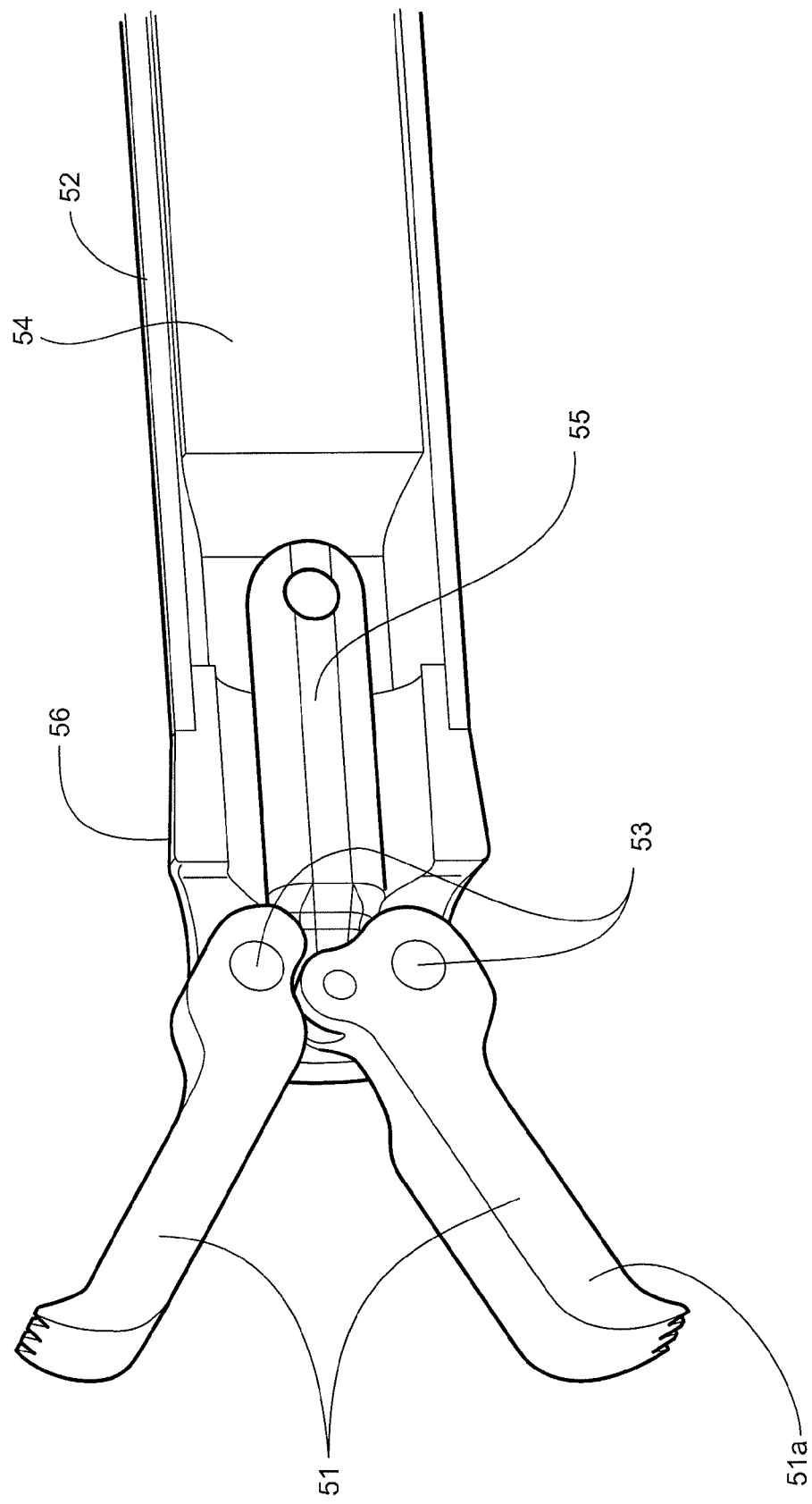
FIG. 5 shows a perspective and cut away view showing an actuation mechanism embodiment.

FIG. 5 shows a perspective and cut away view showing an actuation mechanism embodiment. Depressing the actuation lever (not shown in FIG. 5) leads to the horizontal motion of push rod 54, which is present inside of shaft 52. Push rod's 54 horizontal motion in turn causes the horizontal motion of actuation link 55. In an embodiment, there are two actuation links. Each actuation link 55 when it moves horizontally causes the rotational movement of the respective scraper tip 51 to which it is affixed. The rotational axis for the scraper tips 51 is at pivot points 53. In FIG. 5, the shown actuation link 55 moves scraper tip 51a. The taper 56 can also be seen in FIG. 5.

Figure 6:
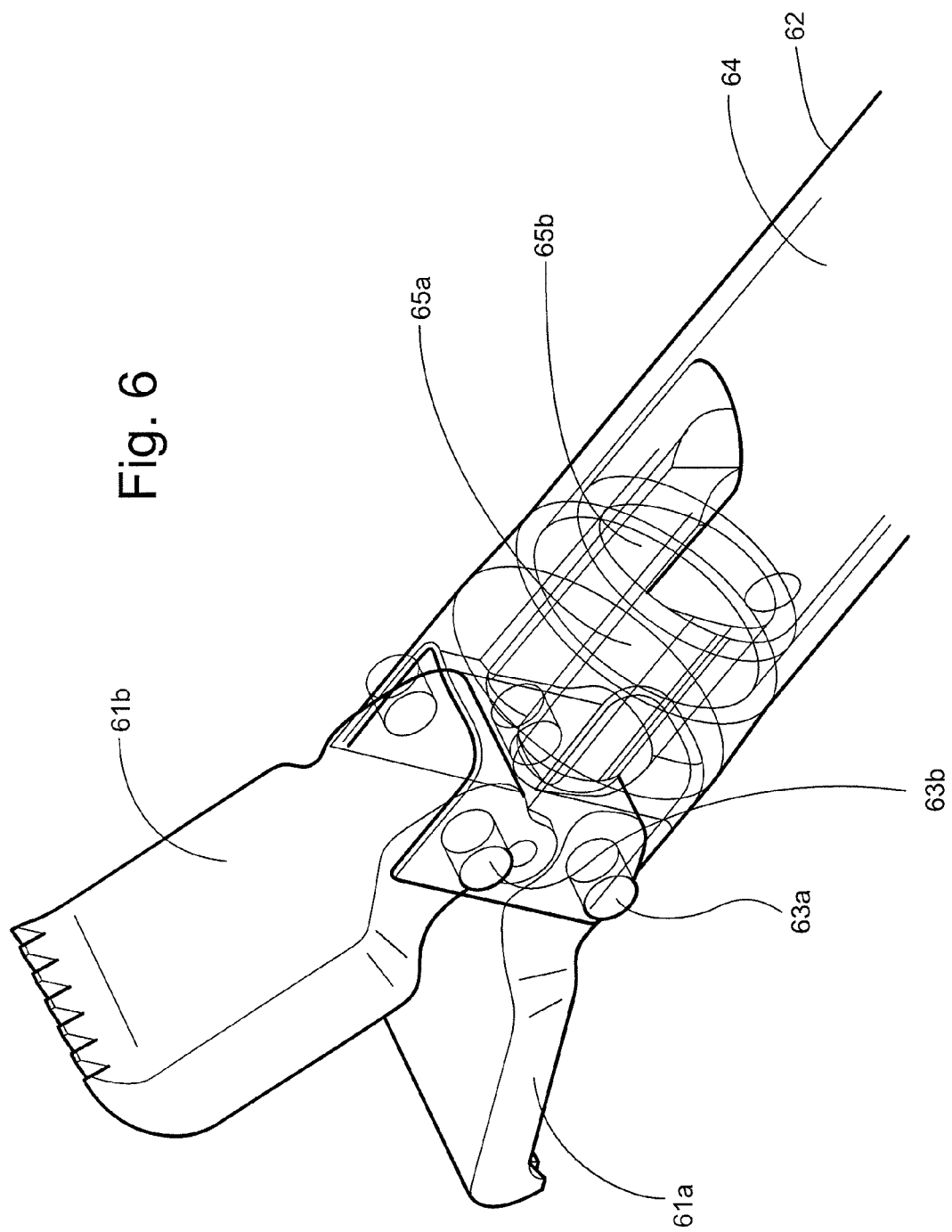
FIG. 6 shows another perspective and transparent view showing an actuation mechanism embodiment.

FIG. 6 shows another perspective and transparent view showing an actuation mechanism embodiment. The push rod 64 moves horizontally inside the shaft 62 after compressing the actuation lever (not shown in FIG. 6), The horizontal movement of the push rod 64 in turn moves actuation links 65a and 65b. The horizontal movement of actuation link 65a causes scraper tip 61a to move rotationally to an open position with pivot point 63a serving as the rotational axis. Likewise, the horizontal movement of actuation link 65b causes scraper tip 61b to move rotationally to an open position with pivot point 63b serving as the rotational axis. In this embodiment the push rod 64 causes actuation links 65a and 65b to move simultaneously allowing scraper tips 61a and 61b to move in unison. When the actuation lever is released (decompressed) the push rod 64 moves in the opposite direction causing the actuation links 65a and 65b to move in the opposite direction, which in turn causes the scraper tips 61a and 61b to close. In an embodiment, the actuation lever (not shown in FIG. 6) can be held in any of a plurality of positions allowing the scraper tips 61a and 61b to attain any of a plurality of positions between the fully open position and the fully closed position.

Figure 7:
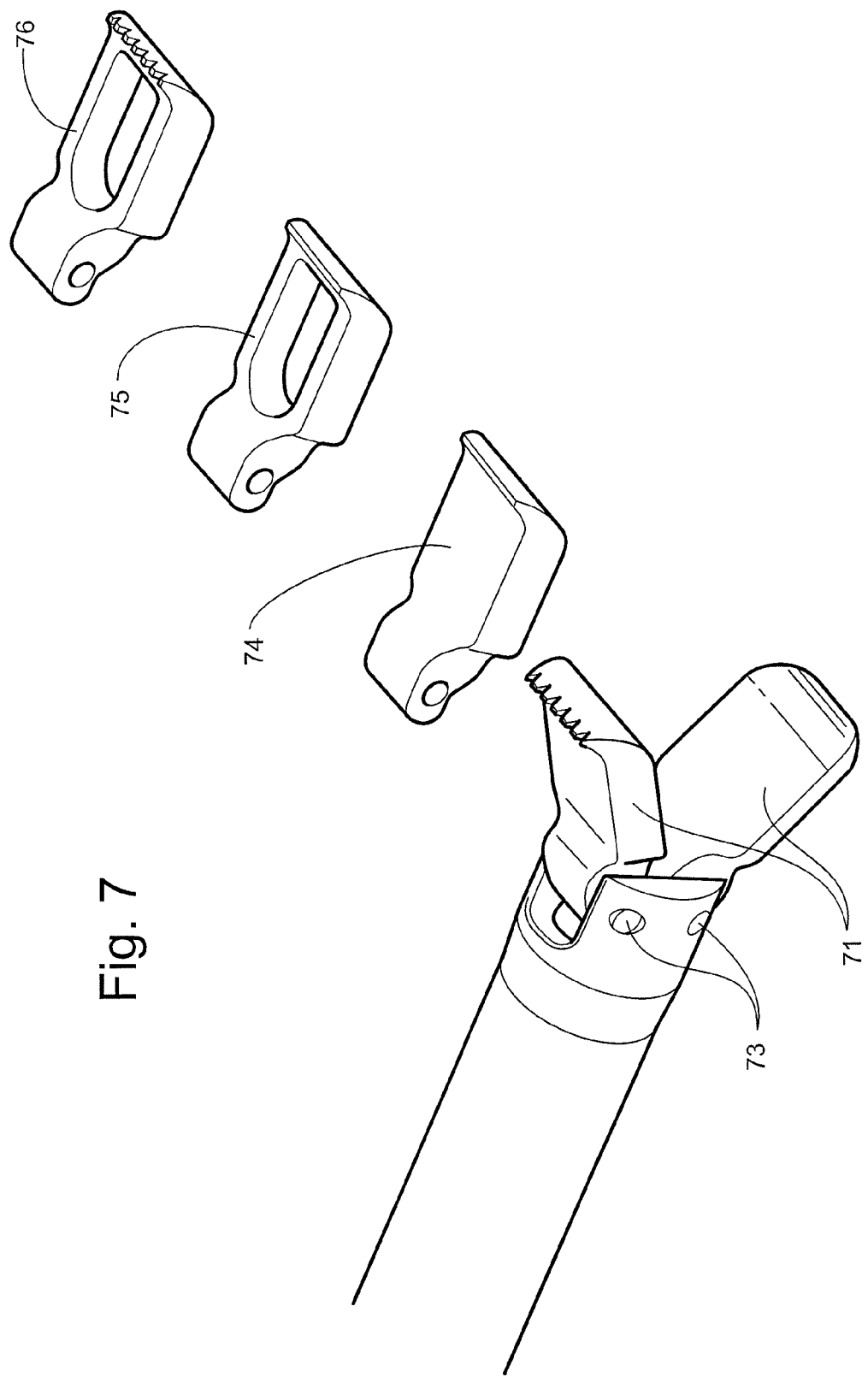
FIG. 7 shows perspective views of the various tips that can be employed on the distal end of the surgical instrument.

FIG. 7 shows perspective views of the various tips that can be employed on the distal end of the surgical instrument. FIG. 7 shows the instrument with scraper tips 71 that are solid serrated tips. The scraper tips are interchangeable via pivot points 73. Accordingly, scraper tips that can be employed include the solid non-serrated scraper tip 74, the hollow center, non-serrated tip 75 and the hollow center, serrated tip 76.

In an embodiment, a tip can also be employed that gives a user information about the distance between two locations. For example, a surgeon might employ a distance measuring tip when inserting the tip end of the instrument between two vertebrae. Once the measuring tips are in a location between the vertebrae, the surgeon would compress the actuation lever until the measuring tips abut against those vertebrae. The amount that the measuring tips are open would give information about the distance between the two vertebrae. By mechanical or electrical means, information may be transmitted to a read out that would give the surgeon the exact distance apart that the two vertebrae are. For example, if a fusion procedure is taking place with bone cement, the surgeon would know the amount of bone cement to insert in the intervertebral disc space. Although this instrument has been discussed in a surgical context, it should be understood that the instrument might also be useful to anyone that needs to measure distances in hard to reach locales (such as mechanics, electricians, plumbers, carpenters, and others).

Figure 8:
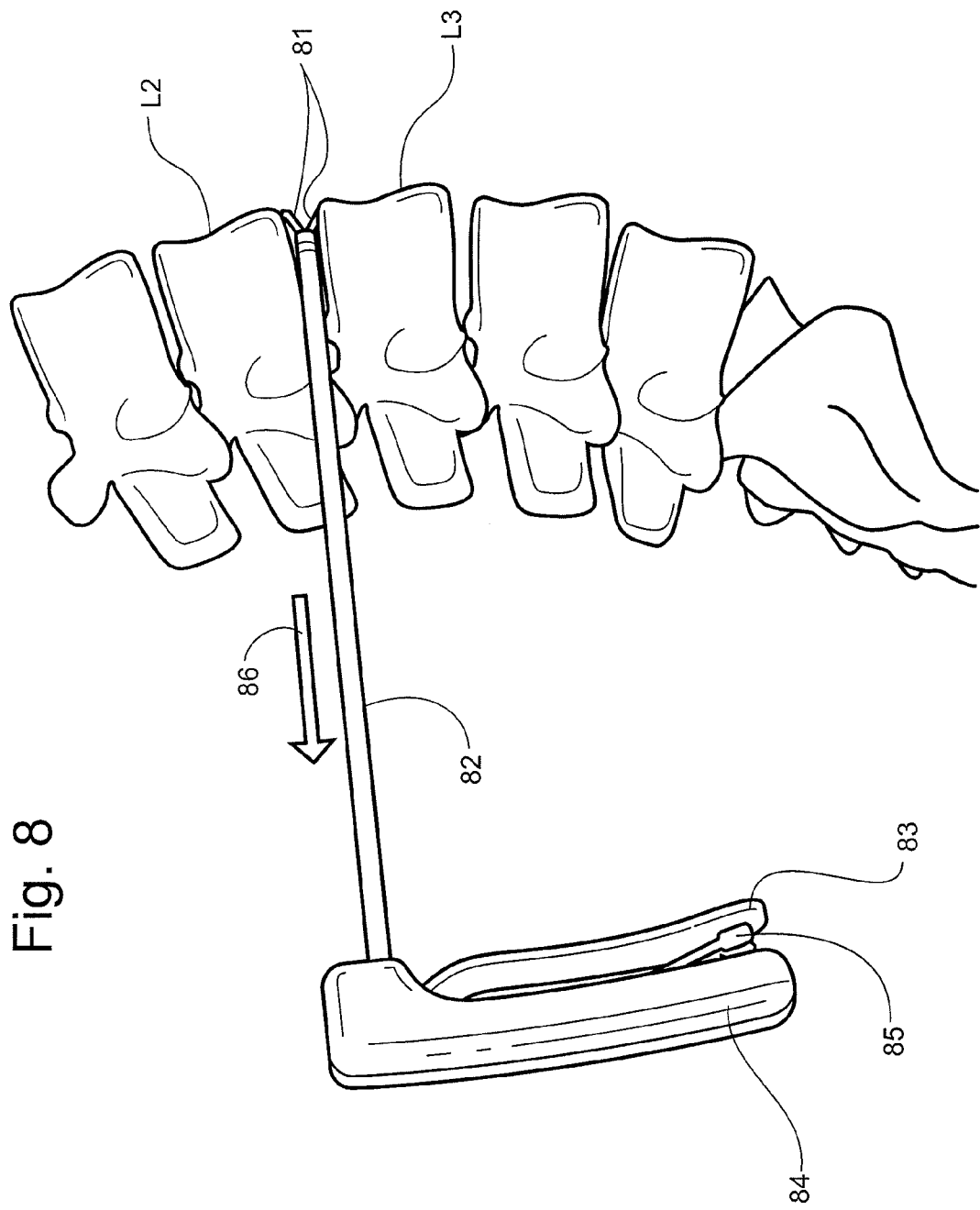
FIG. 8 shows a surgical instrument embodiment positioned in between two endplates of adjacent vertebrae.

FIG. 8 shows a surgical instrument embodiment positioned in between two endplates of adjacent vertebrae L2 and L3. The user holds the instrument by handle 84. Compressing actuation lever 83 causes adjoining piece 85 to move which in turn causes push rod in shaft 82 to move horizontally. The horizontal movement of push rod causes actuation link to also move horizontally, which causes the rotational opening of scraper tips 81. By moving the instrument in the direction shown as 86, the endplates of vertebrae L2 and L3 are scraped. The instrument can be scraped one time in direction 86 or a plurality of times until the desired scraping has been performed. Release (de-compression) of actuation lever 83 allows adjoining piece 85 to return to its open state, causing the movement of push rod and actuation link in the opposite direction, thereby causing scraper tips 81 to go to their closed position. When the scraper tips 81 are in their closed position, this allows the instrument to be withdrawn from the surgical site through the cannula (not shown in figure). The biasing of one scraper tip against the other allows the endplates to be scraped evenly and simultaneously.

FIG. 9 shows a perspective and larger view of the distal end of the instrument between two adjacent vertebrae L4 and L5. The biasing of one scraper tip 91a against the other 91b allows the endplates on adjacent vertebrae L4 and L5 to be scraped effectively, evenly and simultaneously.

The instruments and methods have been described with reference to the examples. It is contemplated and therefore within the scope of the invention that any element that is described anywhere in the above description can be combined with any other element. Moreover, when a range is disclosed, any number that falls within the range is a contemplated endpoint, even if that number is not explicitly disclosed.

Additionally, although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Where methods and steps described above indicate certain events occurring in certain order, those of ordinary skill in the art will recognize that the ordering of certain steps may be modified and that such modification are in accordance with the variations of the invention. Furthermore, certain steps may be performed concurrently in a parallel process when possible, as well as performed sequentially as described above.

Therefore, the above description should not be taken as limiting the scope of the invention but rather the invention should be defined by the below claims.

We claim:

1. An instrument comprising:
an actuation mechanism,
a handle,
a shaft, and
first and second scraper tips, the instrument having a first pivot point extending through the shaft and at least one of the first and second scraper tips about which the first and second scraper tips rotate relative to each other, a second pivot point extending through the shaft and the first scraper tip about which the first scraper tip rotates relative to the shaft and a third pivot point extending through the shaft and the second scraper tip about which the second tip rotates relative to the shaft,
wherein the handle is functionally connected to and positioned at a proximal end of the shaft and the scraper tips are positioned at a distal end of the shaft, and when the activation mechanism is actuated, the scraper tips go from a position that is closed to a position that is at least partially open.

2. The instrument of claim 1, wherein the actuating mechanism comprises an actuation lever, a push rod and one or more actuation links, wherein the actuation lever is functionally connected to the push rod so that when the actuation lever is compressed the push rod moves in a horizontal direction, causing the one or more actuation links to move in a horizontal direction, which causes the scraper tips to rotate from the closed position to the at least partially open position.

3. The instrument of claim 2 comprising two actuation links.

4. The instrument of claim 2, wherein the scraper tips are interchangeable.

5. The instrument of claim 2, wherein the first scraper tip rotates between about 1 and 30 degrees relative to a length of the shaft and the second scraper tip rotates between about −1 and −30 degrees relative to the length of the shaft to move the scraper tips from the closed position to the at least partially open position.

6. The instrument of claim 1, wherein the pivot points contain a means for removing the scraper tips.

7. The instrument of claim 1, wherein the scraper tips each have a hollow center.

8. The instrument of claim 1, wherein the scraper tips are configured to rotate up to 90 and −90 degrees such that the scraper tips are perpendicular to the length of the shaft when in the at least partially open position.

9. An instrument comprising:
an actuation lever, a handle, a shaft, and tips wherein the actuation lever is connected to the handle, the handle is functionally connected to and positioned at a proximal end of the shaft and the tips are positioned at a distal end of the shaft, the tips contain a first and a second tip, wherein when the actuation lever is compressed, the first tip and the second tip go from a position that is substantially parallel to a length of the shaft to a position wherein the first tip rotates between about 1 and 30 degrees relative to the length of the shaft and the second tip rotates between about −1 and −30 degrees relative to the length of the shaft, wherein the instrument includes a first pivot point extending through the shaft and at least one of the first and second scraper tips about which the first and second tips rotate relative to each other, wherein the instrument includes a second pivot point extending through the shaft and the first scraper tip about which the first tip rotates relative to the shaft, and wherein the instrument includes a third pivot point extending through the shaft and the second scraper tip about which the second tip rotates relative to the shaft.

10. The instrument of claim 9, wherein the instrument is part of a spinal surgery kit which comprises one or more members selected from the group consisting of a cannula, an instruction manual, bone cement, expandable balloons, interchangeable tips and other surgical instruments.

11. The instrument of claim 10, further comprising a means of measuring a distance between adjacent vertebrae by positioning the tips in an intervertebral disc space.

12. The instrument of claim 9, wherein the first tip and second tips are a first scraper tip and a second scraper tip, respectively, and the first scraper tip and the second scraper tip have serrated edges.

13. The instrument of claim 12, further comprising a push rod and one or more actuation links, the actuation lever is functionally connected to the push rod, the push rod is functionally connected to the one or more actuation links, and the actuation links are functionally connected to the scraper tips, so that when the actuation lever is compressed, the first tip and the second tip rotates relative to the length of the shaft.

14. The instrument of claim 13, wherein distance between adjacent vertebrae is measured electronically or mechanically.

* * * * *